United States Patent
Sampognaro

(10) Patent No.: US 9,211,099 B2
(45) Date of Patent: Dec. 15, 2015

(54) RADIAL ACCESS METHODS AND APPARATUS

(71) Applicant: G2 Medical, LLC, Monroe, LA (US)

(72) Inventor: Gregory Sampognaro, Monroe, LA (US)

(73) Assignee: G2 Medical, LLC, Monroe, LA (US)

( * ) Notice: Subject to any disclaimer, the term of this patent is extended or adjusted under 35 U.S.C. 154(b) by 0 days.

(21) Appl. No.: 14/166,556

(22) Filed: Jan. 28, 2014

(65) Prior Publication Data

US 2014/0221811 A1    Aug. 7, 2014

Related U.S. Application Data

(60) Provisional application No. 61/850,097, filed on Feb. 7, 2013, provisional application No. 61/962,262, filed on Nov. 4, 2013.

(51) Int. Cl.
| | |
|---|---|
| A61B 6/04 | (2006.01) |
| A61M 5/52 | (2006.01) |
| A61B 6/10 | (2006.01) |
| A61B 6/00 | (2006.01) |

(52) U.S. Cl.
CPC ............... *A61B 6/0428* (2013.01); *A61M 5/52* (2013.01); *A61B 6/107* (2013.01); *A61B 6/4441* (2013.01)

(58) Field of Classification Search
CPC .... A61B 6/0428; A61B 6/107; A61B 6/4441; A61M 5/52
USPC ................................ 5/601, 623; 128/877–878
See application file for complete search history.

(56) References Cited

U.S. PATENT DOCUMENTS

| | | | | | |
|---|---|---|---|---|---|
| 353,049 | A | * | 11/1886 | Barnhart | 108/64 |
| 2,609,261 | A | * | 9/1952 | Parker | 5/646 |
| 3,020,909 | A | | 2/1962 | Stevens | |
| 3,746,332 | A | | 7/1973 | Hakstian | |
| 4,045,011 | A | | 8/1977 | Ford | |
| D287,626 | S | * | 1/1987 | Wilson et al. | D24/183 |
| 4,635,914 | A | * | 1/1987 | Kabanek | 5/630 |
| 4,681,308 | A | * | 7/1987 | Rice | 5/601 |
| 4,698,837 | A | * | 10/1987 | Van Steenburg | 378/208 |
| 4,858,903 | A | | 8/1989 | Tari et al. | |

(Continued)

FOREIGN PATENT DOCUMENTS

| | | |
|---|---|---|
| JP | 2010201025 | 9/2010 |
| WO | WO 2005/096764 | 10/2005 |

OTHER PUBLICATIONS

STARBoard system, *Cardiac Interventions Today*, p. 27, May-Jun. 2014.

*Primary Examiner* — David E Sosnowski
*Assistant Examiner* — Myles Throop
(74) *Attorney, Agent, or Firm* — Levine Bagade Han LLP

(57) ABSTRACT

Radial access methods and apparatus are described for facilitating the securement of the patient's limb for a radial procedure as well as to accommodate for the re-positioning of the patient's body. A radial table assembly may generally comprise a platform defining a surface which is sized to support the limb of the patient, an interface portion attached at a distal end of the platform, wherein the interface portion is radiolucent and extends at a distance from the platform, and a cradle member rotatably connected to the platform at a location proximal to the interface portion. In other variations, the interface portion is reconfigurable relative to the platform such that an angled edge is reversible relative to the platform.

27 Claims, 20 Drawing Sheets

(56) References Cited

U.S. PATENT DOCUMENTS

| | | | |
|---|---|---|---|
| 5,133,097 A * | 7/1992 | Pyles | 5/623 |
| 5,287,575 A | 2/1994 | Allen et al. | |
| 5,864,902 A | 2/1999 | Rogers | |
| 6,154,902 A | 12/2000 | Russillio et al. | |
| 6,195,820 B1 | 3/2001 | Heimbrock et al. | |
| 6,336,412 B2 * | 1/2002 | Heimbrock et al. | 108/42 |
| 6,378,149 B1 | 4/2002 | Sanders et al. | |
| 6,467,487 B1 * | 10/2002 | Rios | 128/869 |
| 6,663,055 B2 | 12/2003 | Boucher et al. | |
| 6,945,252 B2 | 9/2005 | Mengato | |
| 7,017,215 B1 | 3/2006 | Singer et al. | |
| 7,103,932 B1 * | 9/2006 | Kandora | 5/613 |
| 7,395,563 B2 | 7/2008 | Whitmore et al. | |
| 7,823,843 B2 | 11/2010 | Oberlaender et al. | |
| 8,369,933 B2 | 2/2013 | Crisco et al. | |
| 8,590,080 B1 | 11/2013 | Staresinic | |
| 2001/0039680 A1 | 11/2001 | Boucher et al. | |
| 2004/0049851 A1 * | 3/2004 | Jahrling | 5/623 |
| 2004/0133980 A1 * | 7/2004 | Coppens et al. | 5/601 |
| 2005/0052066 A1 | 3/2005 | Wright | |
| 2005/0160533 A1 | 7/2005 | Boucher et al. | |
| 2007/0011814 A1 | 1/2007 | Rotert | |
| 2008/0172791 A1 * | 7/2008 | Walczyk | 5/623 |
| 2010/0305431 A1 | 12/2010 | Crisco et al. | |
| 2012/0138065 A1 | 6/2012 | Campagna | |

* cited by examiner

RADIAL ACCESS METHODS AND APPARATUS

CROSS-REFERENCE TO RELATED APPLICATIONS

This application claims the benefit of priority to U.S. Prov. Pat. App. Ser. Nos. 61/850,097 filed Feb. 7, 2013 and 61/962,262 filed Nov. 4, 2013, each of which is incorporated herein by reference in its entirety.

FIELD OF THE INVENTION

The present invention relates to methods and apparatus for facilitating radial access procedures. More particularly, the present invention relates to methods and apparatus for facilitating radial access procedures when repositioning the patient is needed or desired.

BACKGROUND OF THE INVENTION

Cardiac catheterization procedures generally utilize a catheter passed through a major artery, such as a femoral artery, to access a patient's heart. Yet access to the intravascular and cardiac systems may also be achieved through a radial artery and is generally believed to be more convenient and may also reduce both the length of the procedure and the risk of complications during the procedure. However, cardiac catheterization procedures often require the use of numerous surgical instruments including guidewires, intravascular balloons, stents, etc.

Moreover, imaging systems such as fluoroscopes or other imaging machines are typically utilized during catheterization procedures. Due to the size and weight of these machines, imaging various tissue regions within the patient's body often necessitates re-positioning of the body relative to the imaging system. This requires physically moving the patient's body. However, because of the number of instruments used during a radial access procedure, re-positioning the patient's body is difficult and cumbersome.

Previous devices have been developed to facilitate radial access. Such devices have included the use of boards or surfaces which extend from the platform upon which the patient is positioned. Such boards are typically clamped or otherwise secured to the platform for supporting the patient's limb, such as their arm, to extend from the body to provide radial access. However, such boards are cumbersome to use in a surgical setting and fail to provide a stable platform upon which instruments can be placed.

Other devices have included the use of arm boards or platforms supported by pivoting or jointed arms which can be clamped upon the catheter laboratory table or a separate supporting structure. While such pivoted or jointed arms are able to support a patient's arm for a radial procedure, these devices still fail to provide any stable platform for instruments and further fail to address the need for moving or re-positioning the patient's body relative to an imaging system.

Accordingly, there exists a need for methods and devices which are able to support any number of instruments for radial access as well as facilitate re-positioning of the patient's body during a radial access procedure.

SUMMARY OF THE INVENTION

In accessing a radial vessel, e.g., for an interventional procedure, the limb of the patient, such as an arm, is generally positioned to extend the wrist and expose a radial artery. To facilitate the securement of the patient's limb for a radial procedure as well as to accommodate for the re-positioning of the patient's body, a radial table assembly as described may be utilized. The table assembly may generally comprise a platform defining a surface which is sized to support the limb of the patient, an interface portion attached at a distal end of the platform, wherein the interface portion is radio-lucent and extends at a distance from the platform, and a cradle member rotatably connected to the platform at a location proximal to the interface portion. In other variations, the interface portion is reconfigurable relative to the platform such that an angled edge is reversible relative to the platform.

The cradle assembly itself may be generally comprised of a cradle member which is configured to receive and support the limb of the patient, a connection interface configured to rotatably secure the assembly to a first platform, and a support arm rotatably extending from the connection interface and rotatably coupled to the cradle member, wherein a position and an orientation of the cradle member is dependent upon a position and an orientation of a second platform.

In use, one method for positioning the patient body with respect to the radial table assembly may generally comprise positioning the limb of the patient body upon the cradle member which is movably attached to a first platform sized to support the limb, moving a second platform upon which the patient body is placed, where the second platform is in proximity to the first platform, and moving the cradle member relative to the first platform in a manner corresponding to a movement of the second platform such that a position or orientation of the cradle member is dependent upon a position or orientation of the second platform when the limb is positioned upon the cradle member.

One example of a radial table assembly may generally comprising a back table supported by one or more legs, a radial table portion extending from the back table, and an interface portion further extending from the radial table portion, e.g., in a cantilevered manner The interface portion may define an angled edge which allows for the table assembly to be positioned relatively at an angle and in close proximity to or adjacent to a catheter laboratory table and provide a platform upon which the patient's limb (such as the arm) may be extended from the patient body positioned upon the table. The table assembly may provide surgeons and practitioners a comfortable way to facilitate procedures, e.g., angiography, percutaneous interventions, etc., through the radial artery.

The back table may comprise a surgical table or platform and the radial table portion may be attached to a distal edge of the back table along an optionally hinged or pivoting interface and having a width of, e.g., 12-48 inches or more, and a length of, e.g., up to 20 inches or longer. The interface portion may be secured at a distal end of the radial table portion also along an optionally hinged or pivoting interface and may have a similar width as the radial table portion. The interface portion may extend at a distance and terminate at its distal end at the angled edge which may have an angle ranging anywhere from, e.g., 10 degrees and up to 90 degrees (or more particularly 45-55 degrees), relative to the length of the table assembly. While each of the back table and radial table portion may be comprised of various materials which are radio-opaque, e.g., stainless steel, the interface portion may be comprised of a radio-lucent material which is optionally anti-bacterial or able to be disinfected, e.g., various polycarbonate materials such as Lexan® (SABIC Innovative Plastics), ultra-high-molecular-weight polyethylene (UHMW), etc. Having the interface portion comprised of a radio-lucent material may allow for an imaging device such as a fluoroscope (or any other suitable imaging device) to penetrate and image the proximal upper sections of the patient's limb, if needed.

A cradle assembly may be rotatably secured to the radial table assembly within any one of the connection interfaces which may be aligned along, e.g., the proximal edge of the radial table portion. The cradle assembly may be optionally positioned in any of the connection interfaces depending upon the positioning of the patient body along the catheter laboratory table. The cradle assembly itself may generally comprise a cradle member having a length of, e.g., up to 10 inches or more, and a width of, e.g., 6 inches or more, and which is configured to define a channel to comfortably receive the patient's wrist, forearm, and hand. An optional proximal cradle member may extend adjustably via an extension arm from the cradle member to support the patient's upper arm if needed or desired. The cradle member and optional proximal cradle member may each be fabricated from either a radio-opaque material (such as stainless steel) or from a radio-lucent material (such as polycarbonate) to further allow for imaging of the forearm and hand of the patient if also desired.

The cradle assembly may define two points of rotation or articulation to enable the rotation of the cradle member relative to a support arm which couples the cradle assembly to the connection interface and to also enable the rotation of the support arm relative to the connection interface and radial table. With the patient body positioned upon the catheter laboratory table, the limb and particularly the hand and wrist may be extended and secured upon a cradle member with the patient's fingers optionally secured to the distal end of the cradle member to extend the wrist. With the limb secured and optionally draped, the radial artery may be readily accessed by any number of percutaneous access or surgical procedures. The surgeon and/or practitioner may be positioned between the catheter laboratory or operating table and the radial table assembly while any number of instruments or interventional tools may be placed or extended upon the radial table portion and/or back table.

However, if the patient body requires repositioning relative to the imaging device positioned above and below the patient and laboratory table, the laboratory table may be translated either along its length or width while keeping the limb secured to the cradle member. Hence, as the patient body moves relative to the imaging device and relative to the radial table assembly, the patient's limb may also be repositioned in a manner corresponding to the repositioning of the patient body due to the rotation of cradle member (and the hand and wrist positioned upon the cradle member) relative to the support arm and also the rotation of the support arm relative to the radial table portion without interference with the surgeon or practitioner. These two points of rotation of the cradle member and the support arm relative to the radial table may allow for a full 360 degrees or movement. Alternatively, the rotation of one or both of the cradle member and support arm relative to the radial table portion may be limited to rotate within specified ranges, if so desired. In either case, because the orientation of the patient's limb may be automatically maintained relative to the patient's body despite any translation of the body relative to the imaging device and/or radial table assembly, any instruments or tools extending from the patient's limb and laid upon the back table may be left in place rather than moved to accommodate movement of the patient body.

Because the radial table assembly may be utilized with a number of different imaging devices, the assembly may be designed to accommodate an imaging system such as a fluoroscope. Such systems typically utilize a C-arm having a detector and x-ray transmitter positioned in apposition to one another at either end of the C-arm. While the imaging system is generally stationary relative to the laboratory table and radial table assembly, the C-arm may be rotatably adjustable for obtaining images of the underlying patient body at various angles. To accommodate such movement of the imaging system, the radial table assembly may be configured to have the radial table portion and interface portion extend at a distance, e.g., anywhere from a foot or up to several feet (or more particularly between 5-6 feet), from the back table in a cantilevered manner to provide for sufficient clearance distance beneath the table in the event that the transmitter (or any other instrument) is positioned beneath the assembly. This cantilevered feature may be incorporated into any of the various embodiments of the table assembly shown or described herein. Measurements and dimensions with respect to the radial table assembly are provided as illustrative examples and may be varied or customized to suit any number of patients as desired.

Because the interface portion defines an angled edge, the interface portion may be adjustably attached to the radial table portion. Yet another feature may include the radial table portion being retractably folded along its interface relative to the back table. Other variations of the radial table may include embodiments where the radial table may be secured or clamped directly to the catheter laboratory table via one or more securement mechanisms (e.g., clamps, etc.) aligned along the angled edge. While other variations include radial table assemblies which may be secured to a separate back table.

Additional features and/or accessories may be utilized in combination. For instance, a radiation shield may be attached along the radial table edge. The radiation shield may be attached along any of the edges of the table assembly in proximity to the surgeon or practitioner to provide for additional shielding against, e.g., x-rays, which may be emitted by imaging devices typically used to image the patient's body. Other features may include one or more cushion supports which are configured and shaped for use along the cradle member may be provided with the radial table assembly or separately. Additionally, surgical drapes configured for use with the table assembly or any number of instruments or displays which are positionable upon the back table or radial table may also be provided, if so desired. All or any one of these accessories may be provided in a kit along with the radial table assembly or they may be provided separately.

DETAILED DESCRIPTION OF THE INVENTION

In accessing a radial vessel, e.g., for an interventional procedure, the limb of the patient is typically extended away from the body and secured to provide a stable insertion pathway for any number of instruments such as catheters, guidewires, intravascular balloons, stent scaffolds, etc. The limb of the patient, such as an arm, is generally positioned to extend the wrist and expose a radial artery.

Figure 1:
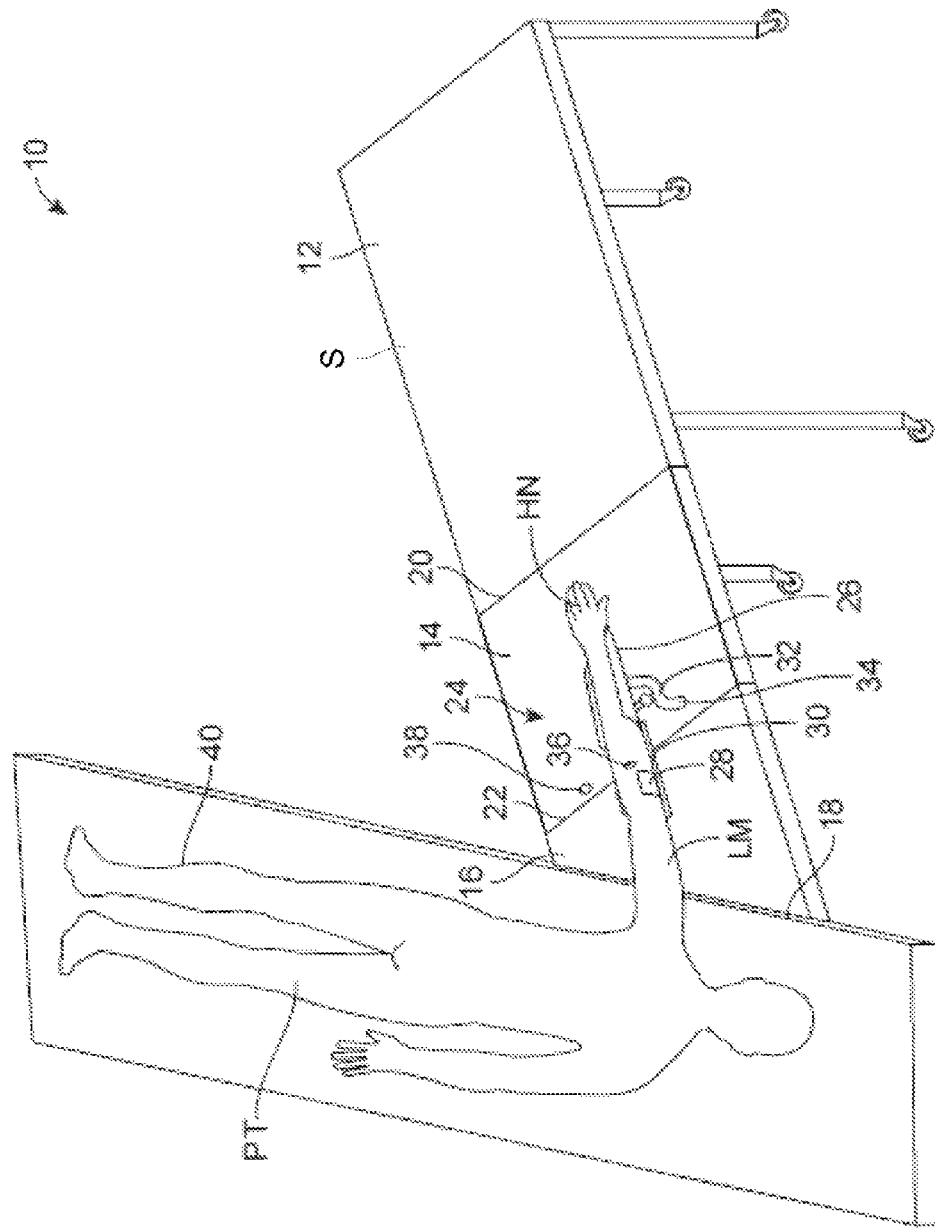
FIG. 1 shows a perspective view of one variation of a radial access table positioned in proximity to a patient platform and having a rotatable support assembly for the patient's arm.

One example of a radial table assembly 10 is illustrated in the perspective view of FIG. 1 which shows the table assembly 10 generally comprising a back table 12 supported by one or more legs, a radial table portion 14 extending from the back table 12, and an interface portion 16 further extending from the radial table portion 14, e.g., in a cantilevered manner. The interface portion 16 may define an angled edge 18 which allows for the table assembly 10 to be positioned relatively at an angle and in close proximity to or adjacent to a catheter laboratory table 40 and provide a platform upon which the patient's limb LM (such as the arm) may be extended from the patient body PT positioned upon the table 40. The table assembly 10 may provide surgeons and practitioners a comfortable way to facilitate procedures, e.g., angiography, percutaneous interventions, etc., through the radial artery.

The back table 12 may comprise a surgical table or platform defining a surface S and the radial table portion 14 may be attached to a distal edge of the back table 12 along an optionally hinged or pivoting interface 20 and having a width of. e.g., 12-48 inches or more, and a length of, e.g, up to 20 inches or longer. The interface portion 16 may be secured at a distal end of the radial table portion 14 also along an optionally hinged or pivoting interface 22 and may have a similar width as the radial table portion 14. The interface portion 16 may extend at a distance and terminate at its distal end at the angled edge 18 which may have an angle ranging anywhere from, e.g., 10 degrees and up to 90 degrees (or more particularly 45-55 degrees), relative to the length of the table assembly 10. While each of the back table 12 and radial table portion 14 may be comprised of various materials which are radio-opaque, e.g., stainless steel, the interface portion 16 may be comprised of a radio-lucent material which is optionally anti-bacterial or able to be disinfected, e.g., various polycarbonate materials such as Lexan® (SABIC Innovative Plastics), ultra-high-molecular-weight polyethylene (UHMW), etc. Having the interface portion 16 comprised of a radio-lucent material may allow for an imaging device such as a fluoroscope (or any other suitable imaging device) to penetrate and image the proximal upper sections of the. patient's limb LM, if needed.

A cradle assembly 24 may be rotatably secured to the radial table assembly 10 within any one of the connection interfaces 34, 36, 38 which may be aligned along, e.g., the proximal edge of the radial table portion 14 as shown. The cradle assembly 24 may be optionally positioned in any of the connection interfaces 34, 36, 38 depending upon the positioning of the patient body PT along the catheter laboratory table 40. The cradle assembly 24 itself may generally comprise a cradle member 26 having a length of, e.g., up to 10 inches or more, and a width of, e.g., 6 inches or more, and which is configured to define a channel to comfortably receive the patient's wrist, forearm, and hand HN. An optional proximal cradle member 28 may extend adjustably via an extension arm 30 from the cradle member 26 to support the patient's upper arm if needed or desired. The cradle member 26 and optional proximal cradle member 28 may each be fabricated from either a radio-opaque material (such as stainless steel) or from a radio-lucent material (such as polycarbonate) to further allow for imaging of the forearm and hand of the patient if also desired.

The cradle assembly 24 may define two points of rotation or articulation to enable the rotation of the cradle member 26 relative to a support arm 32 which couples the cradle assembly 24 to the connection interface 34 and to also enable the rotation of the support arm 32 relative to the connection interface 34 and radial table 14. With the patient body PT positioned upon the catheter laboratory table 40, the limb LM and particularly the hand and wrist may be extended and secured upon a cradle member 26 with the patient's fingers optionally secured to the distal end of the cradle member 26 to extend the wrist. With the limb LM secured and optionally draped, the radial artery may be readily accessed by any number of percutaneous access or surgical procedures. The surgeon and/or practitioner may be positioned between the catheter laboratory table 40 (or operating table) and the radial table assembly 10 while any number of instruments or interventional tools may be placed or extended upon the radial table portion 14 and/or back table 12.

However, if the patient PT body requires repositioning relative to the imaging device positioned above and below the patient PT and laboratory table 40, the laboratory table 40 may be translated either along its length or width while keeping the limb LM secured to the cradle member 26. Hence, as the patient body PT moves relative to the imaging device and relative to the radial table assembly 10, the patient's limb LM may also be repositioned in a manner corresponding to the repositioning of the patient body PT due to the rotation of cradle member 26 (and the hand and wrist positioned upon the cradle member 26) relative to the support arm 32 and also the rotation of the support arm 32 relative to the radial table portion 14 without interference with the surgeon or practitioner. These two points of rotation of the cradle member 26 and the support arm 32 relative to the radial table may allow for a full 360 degrees or movement. Alternatively, the rotation of one or both of the cradle member 26 and support arm 32 relative to the radial table portion 14 may be limited to rotate within specified ranges, if so desired. In either case, because the orientation of the patient's limb LM may be automatically maintained relative to the patient's body PT despite any translation of the body PT relative to the imaging device and/or radial table assembly 10, any instruments or tools extending from the patient's limb LM and laid upon the back table 12 may be left in place rather than moved to accommodate movement of the patient body PT.

Figure 2A:
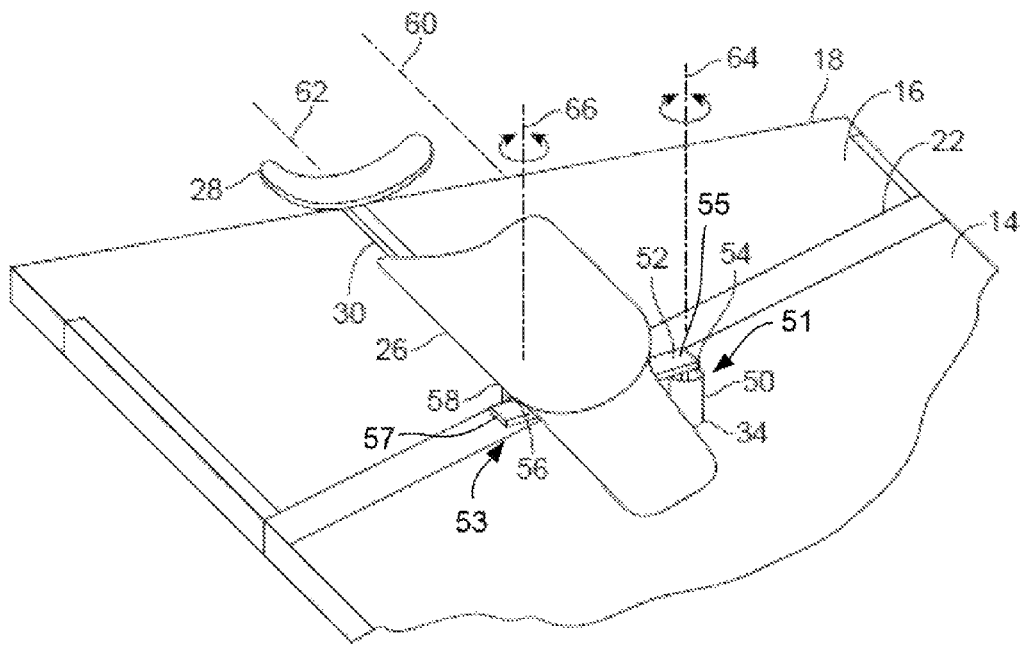
FIGS. 2A and 2B illustrate another variation of a support assembly rotatably mounted upon the radial access table.
Figure 2B:
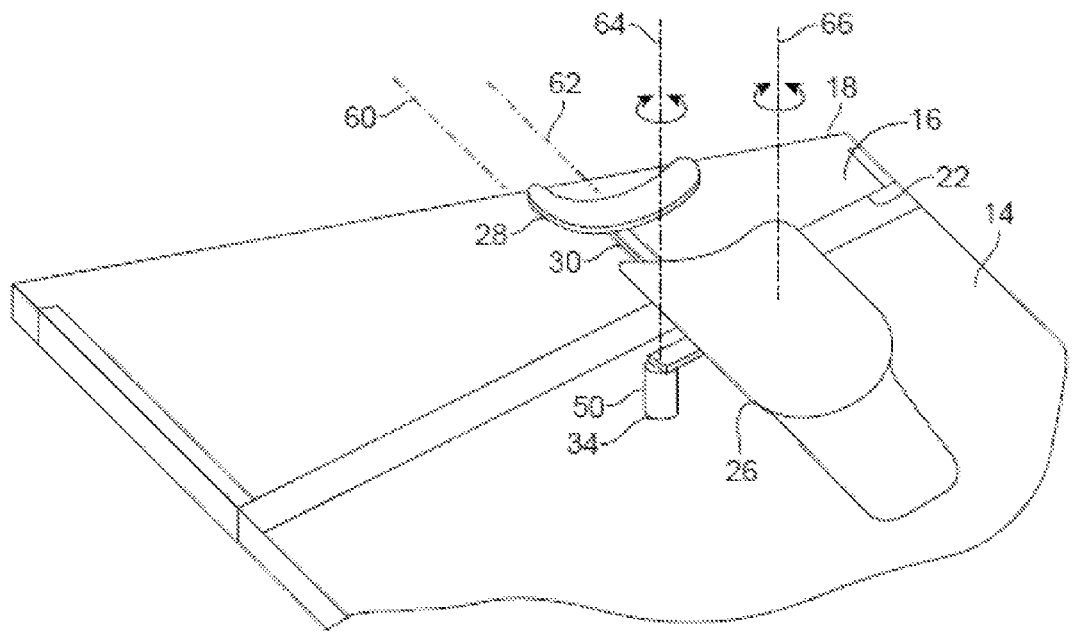

FIGS. 2A and 2B show perspective detail views (without patient limb LM shown for clarity) of another variation of the cradle assembly to illustrate its relative movement, in this variation, the cradle member 26 may be coupled. to the radial table portion 14 via a support arm 52 (described in further detail below) having an insertion rod extending perpendicularly relative to the support arm 52. A receiving support. 50 which defines a receiver opening 54 for receiving the insertion rod of the support arm 52 may be secured within the connection interface 34 to form a first pivot 51 at a proximal end 55 of the support arm 52 in this variation. Although a single connection interface 34 is shown in this example, any number of additional connection interfaces may be optionally placed at different locations along the radial table portion 14 to accommodate various orientations. A second receiver support 56 may extend from the cradle member 26 and define a second receiver opening 58 for receiving a second perpendicular insertion rod extending from the support arm 52 to form a second pivot 53 at a distal end 57 of the support arm 52 in this variation.

The radial table assembly centerline 60 is shown and the cradle assembly centerline 62 is also shown for illustrative purposes. FIG. 2A shows how the cradle assembly centerline 62 is initially oriented relative to the radial table assembly centerline 60. As the laboratory table 40 and the patient body PT is repositioned relative to a stationary imaging device and stationary radial table assembly 10, the patient's arm may correspondingly cause the cradle member 26 to rotate about its cradle axis of rotation 64 as well as the cradle member axis of rotation 66. Even in its reoriented position shown in FIG. 2B, the orientation of the cradle assembly centerline 62 is still maintained relative to the radial table assembly centerline 60.

Figure 3A:
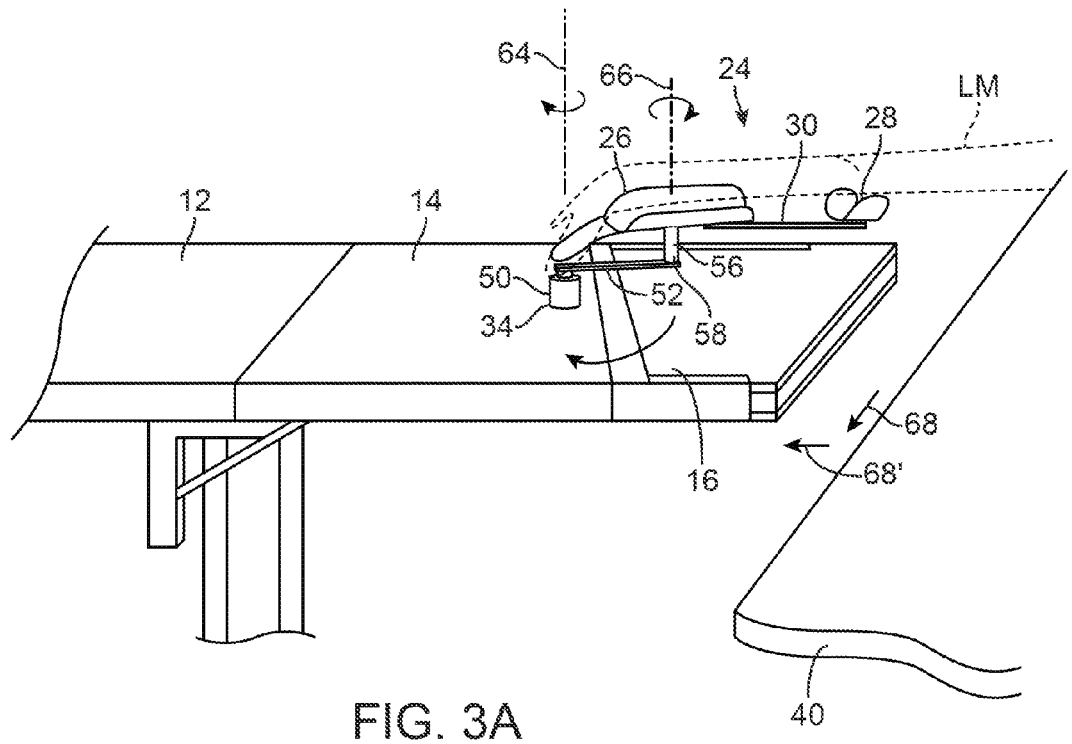
FIGS. 3A and 3B show perspective views of a patient's arm extending from a catheter laboratory table while supported upon the support assembly and further illustrating how the patient's arm is movable relative to the stationary radial access table in a manner corresponding to a movement of the catheter laboratory table.
Figure 3B:
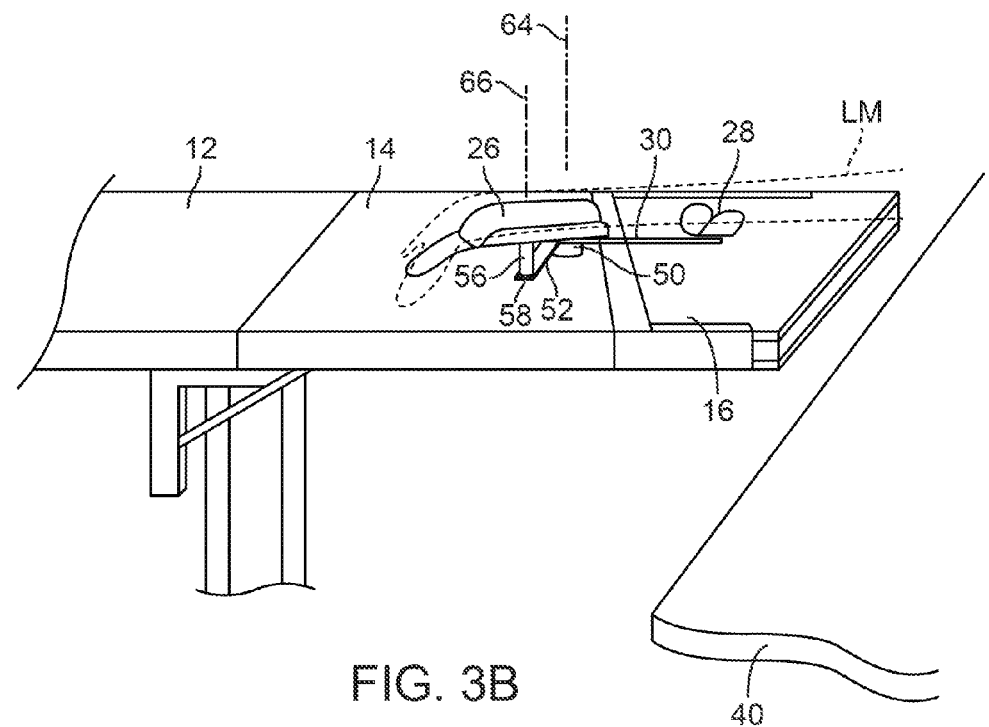

Another example is shown in the perspective views of FIGS. 3A and 3B which illustrate the radial access table assembly 10 placed against or in proximity to the laboratory table 40. An example of the patient's limb LM extending from the laboratory table 40 may be seen initially secured upon the cradle member 26. As the laboratory table 40 is translated, e.g., in a direction of motion 68 and 68', the cradle member 26 may correspondingly rotate about its cradle axis of rotation 64 and its cradle member axis of rotation 66 such that the cradle member 26 is repositioned relative to the radial table portion 14 but an orientation of the limb LM is maintained relative to the patient body PT by the maintained orientation of the cradle member 26.

Figure 4:
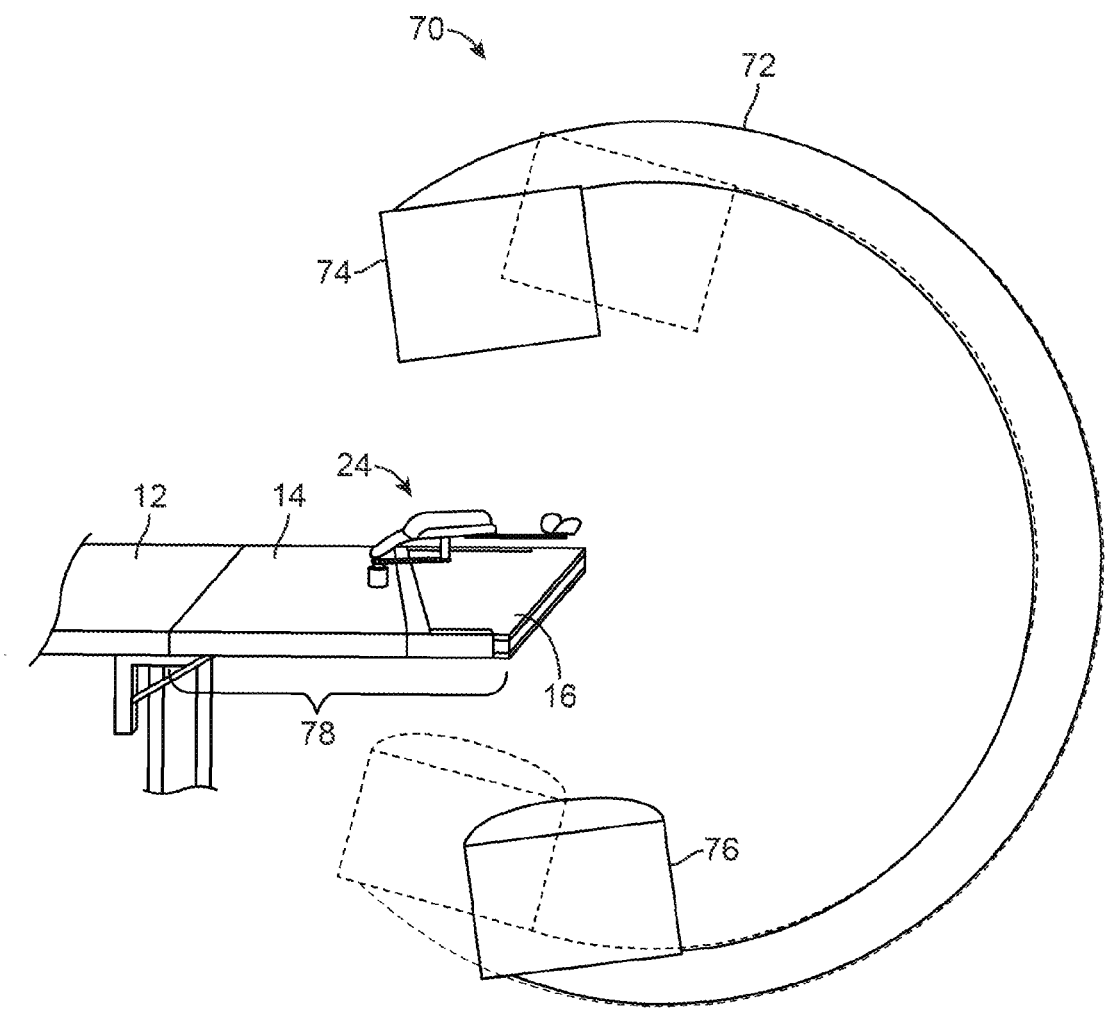
FIG. 4 shows an illustrative view of how an imaging system such as a fluoroscopy device is positionable relative to the radial access table.

Because the radial table assembly 10 may be utilized with a number of different imaging devices, the assembly 10 may be designed to accommodate an imaging system 70 such as a fluoroscope, as shown in the perspective view of FIG. 4. Such systems 70 typically utilize a C-arm 72 having a detector 74 and x-ray transmitter 76 positioned in apposition to one another at either end of the C-arm 72. While the imaging system 70 is generally stationary relative to the laboratory table 40 and radial table assembly 10, the C-arm 72 may be rotatably adjustable for obtaining images of the underlying patient body at various angles. To accommodate such movement of the imaging system 70, the radial table assembly 10 may be configured to have the radial table portion 14 and interface portion 16 extend at a distance, e.g., anywhere from a foot or up to several feet (or more particularly between 5-6 feet), from the back table 12 in a cantilevered manner to provide for sufficient clearance distance 78 beneath the table in the event that the transmitter 76 (or any other instrument) is positioned beneath the assembly 10. This cantilevered feature may be incorporated into any of the various embodiments of the table assembly shown or described herein. Measurements and dimensions with respect to the radial table assembly are provided as illustrative examples and may be varied or customized to suit any number of patients as desired.

Figure 5:
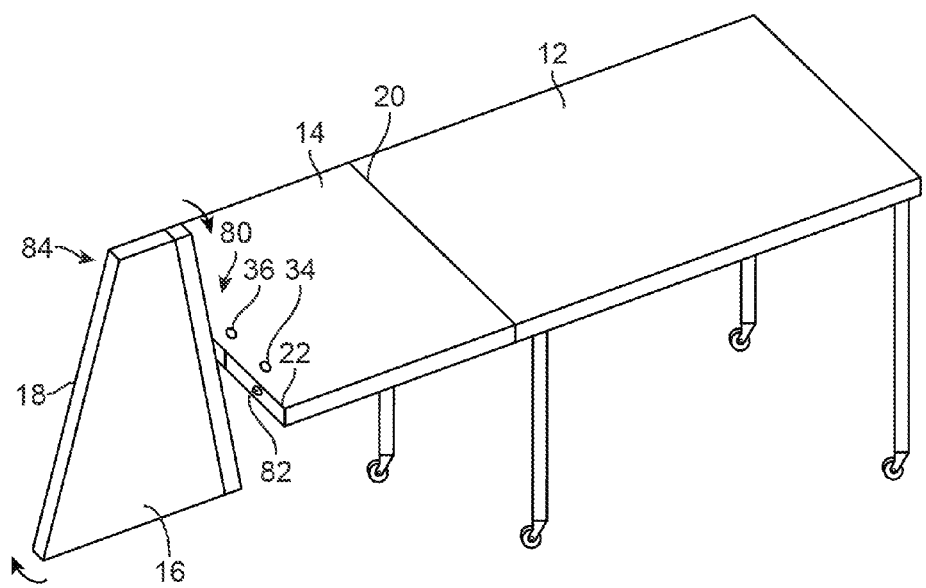
FIG. 5 shows a perspective view of how an interface portion of the radial access table is reconfigurable relative to the remainder of the table.

Another feature of the table assembly 10 is shown in the perspective view of FIG. 5 which illustrates a reconfigurable interface portion 16. Because the interface portion defines an angled edge 18, the interface portion 16 may be adjustably attached to the radial table portion 14. While the interface portion 16 may be entirely removable from the radial table portion 14, the variation shown illustrates an interface portion 16 which may be rotatably coupled to the radial table portion 14. The interface portion 16 may be coupled to the radial table portion via a point of rotation 80 which allows the angled edge 18 to be reconfigured into an opposite direction to enable the placement of the radial table assembly 10 on the opposite side of the laboratory table 40, e.g., from a left side to a right side of the laboratory table 40, to facilitate access through either arm of the patient. One or more mating features 82, 84 may project along the interface 22 to secure the interface 22 and prevent free rotation of the interface portion 16 relative to the radial table portion 14 during use.

Figure 6:
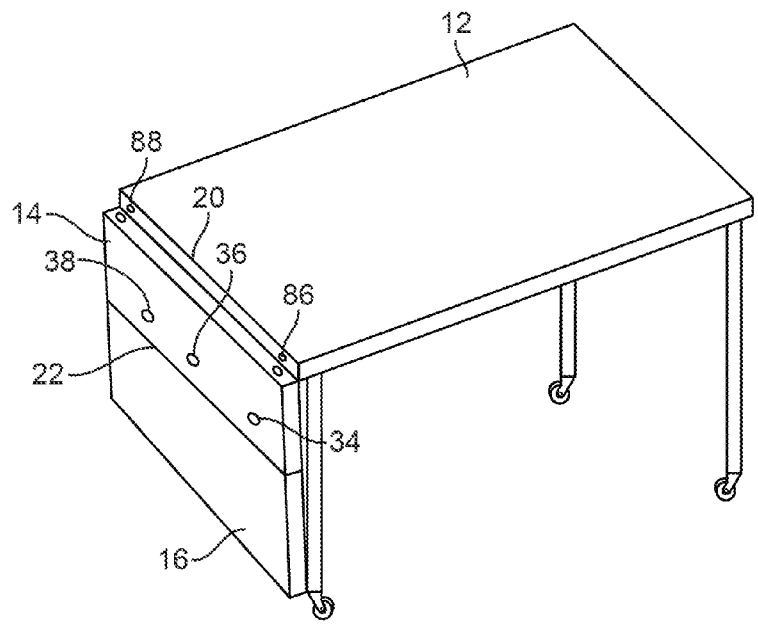
FIG. 6 shows a perspective view of another variation in which an interface portion and radial table is reconfigurable to collapse relative to the back table.

Yet another feature is shown in the perspective view of FIG. 6 which shows how the radial table portion 14 may be retractably folded along its interface 20 relative to the back table 12. By unlocking the radial table portion 14 from the back table 12, both the table portion 14 and interface portion 16 may be folded via one or more pivots or hinges along interface 20 for storage or in the event that only the back table 12 is to be utilized for a procedure. One or more radial table mating feature 86, 88 may project along the interface 20 to secure the interface 20 between the radial table portion 14 and the back table 12 when in use.

It is intended that both the rotatable interface portion 16 shown in FIG. 5 as well as the pivoting radial table portion 14 may be incorporated together or individually with any of the embodiments described herein and in any combination as practicable. For instance, each of the features shown and described in FIGS. 3A-3B as well as FIGS. 4-6 may be combined into a single embodiment of a radial table assembly, if so desired.

Figure 7:
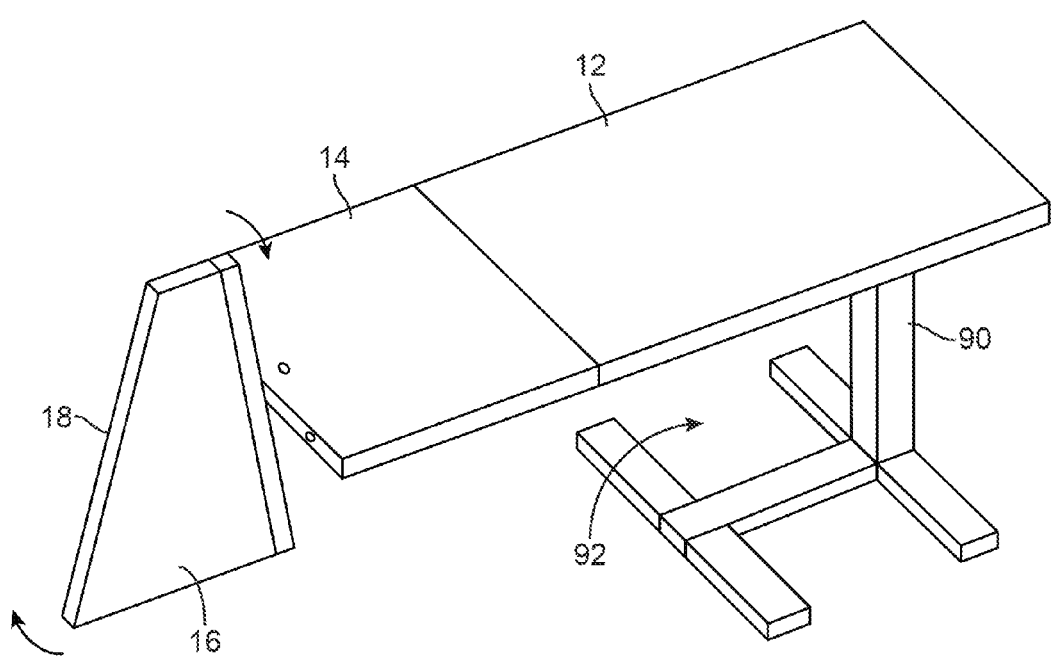
FIG. 7 shows a perspective view of another variation illustrating the back table supported by a table leg which provides sufficient clearance beneath the table.

FIG. 7 shows a perspective view of yet another variation of the radial table assembly. In this example, the back table 12 may utilize a single table support 90 which projects perpendicularly from a distal end of the back table 12. Positioning of the table support 90 at the distal end may provide for sufficient clearance space 92 beneath the radial table portion 14 and interface portion 16 as well as beneath the back table 12 as well.

Figure 8:
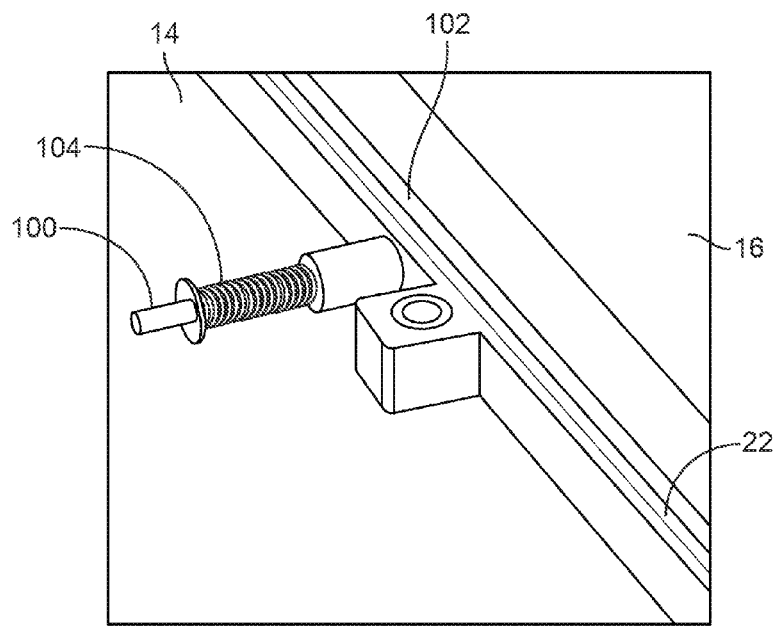
FIG. 8 shows a perspective view of an example of how the interface portion may be secured to the radial table portion.

FIG. 8 shows a perspective view of one variation for implementing the pivoting point of rotation shown above in FIG. 5 between the interface portion 16 and radial table portion 14. A support member 100 may extend rigidly from the interface portion 16 for rotatable insertion within a receiving collar 102 defined along the radial table portion. A distal portion of the support member 100 may extend beyond the collar 102 to provide for a biasing member 104, e.g., a spring, to be secured therebetween. The biasing member 104 may provide for a biasing force to keep the interface portion 16 against the radial table portion 14 while still allowing for the rotation of support member 100 and interface portion 16 about collar 102.

Figure 9:
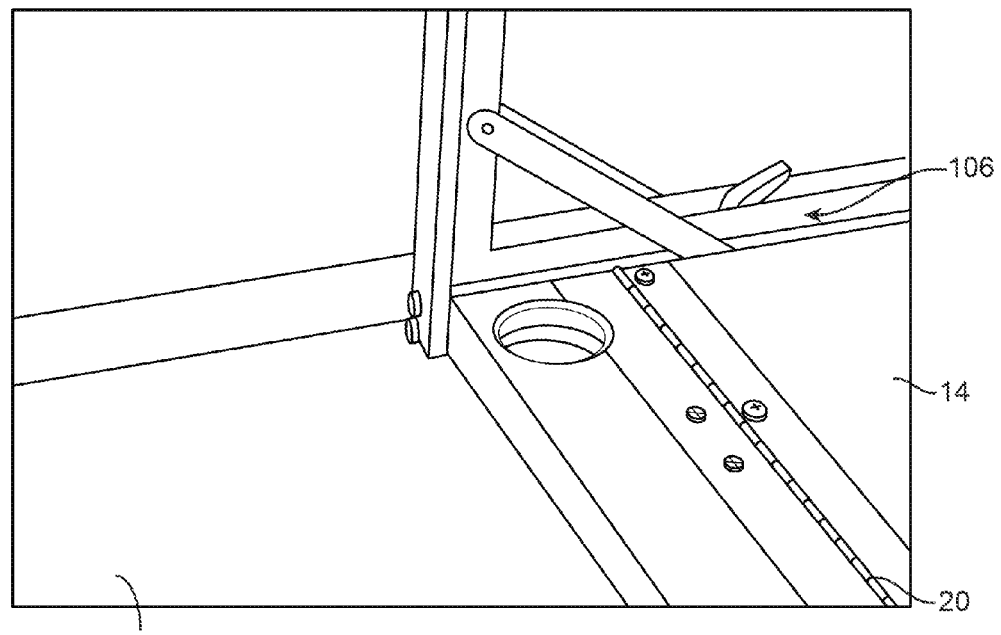
FIG. 9 shows a perspective view of an example of how the radial table and interface portion may be reconfigurably secured to the back table.
Figure 10:
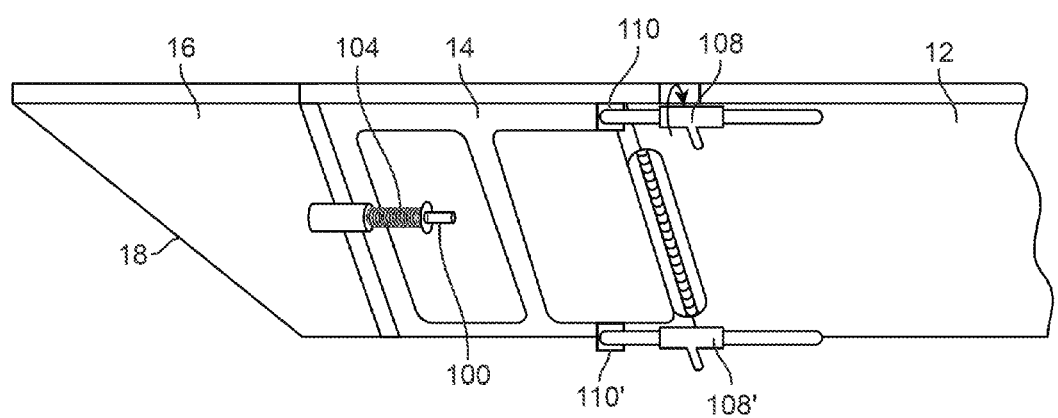
FIG. 10 shows a perspective view of another example illustrating how the radial table and interface portion may be reconfigurably secured to the back table.

Aside from the rotation of the interface portion 16, FIG. 9 shows a perspective view of one variation for implementing the pivoting interface between the radial table portion 14 and the back table 12 shown above in FIG. 6. In this variation, locking brackets 106 may be secured between the radial table portion 14 and back table 12. Such brackets 106 may be hinged to selectively provide for repositioning of the radial table portion 14 in its cantilevered position as well as it retracted position. FIG. 10 shows another variation for implementing a pivoting interface between the radial table portion 14 and the back table 12. In this variation, one or more sliding bolts 108, 108' may retractably extend from or to the back table 12 for securement within a corresponding receiving channel 110, 110' defined along either the radial table portion 14 or back table 12. When the one or more sliding bolts 108, 108' are retracted, the radial table portion 14 may be lowered but when the one or more sliding bolts 108, 108' are extended, the radial table portion 14 may be locked into its cantilevered configuration.

Figure 11:
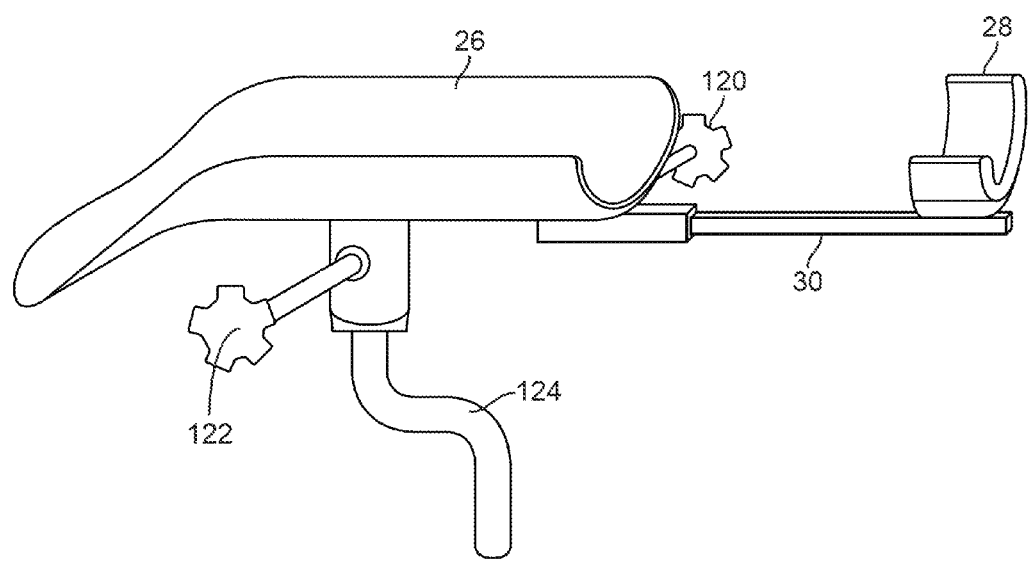
FIG. 11 shows a perspective view of another variation of a support assembly.

Turning now to the cradle assembly, FIG. 11 shows a perspective view of another variation of the cradle assembly having one or more optional locking controls 120, 122. Such a locking control 122 may provide for either free or tensioned rotation of the cradle member 26 or full locking of the cradle member 26 if needed. The locking control 120 may also provide for selective locking of the extension arm 30 when adjusting a position of the proximal cradle member 28. Also shown in this variation is a curved support arm 124 which may rotatably extend between cradle member 26 and the connection interface defined within the radial table portion. The support arm 124 may be an arcuate arm which can be curved and lengthened to vary the height of the cradle member 26 from the underlying radial table portion 14.

Figure 12A:
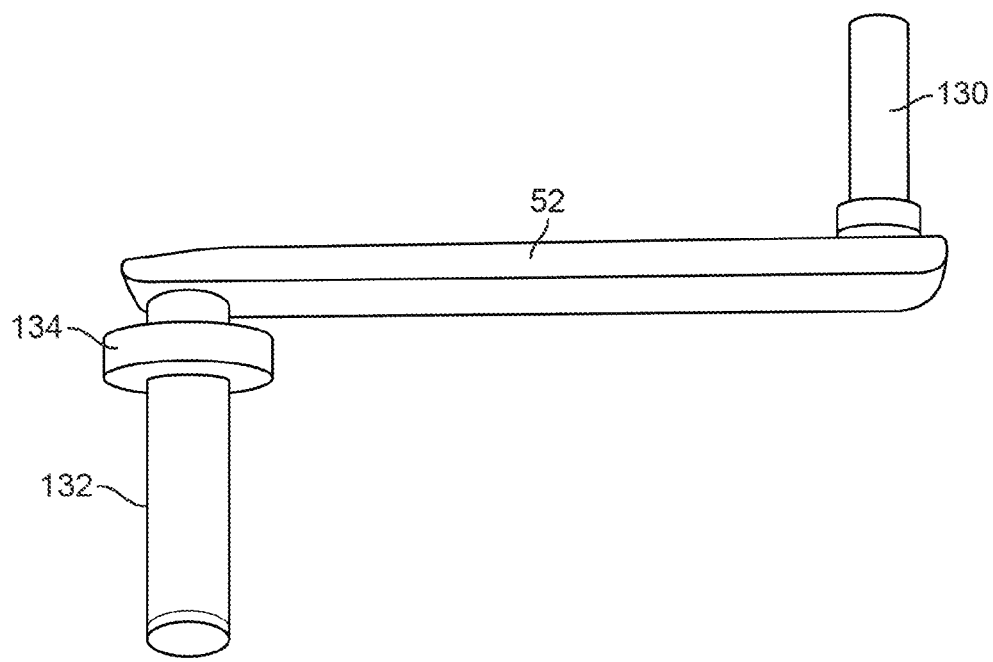
FIGS. 12A and 12B show side and end views of a support arm variation for rotatably securing the support assembly.
Figure 12B:
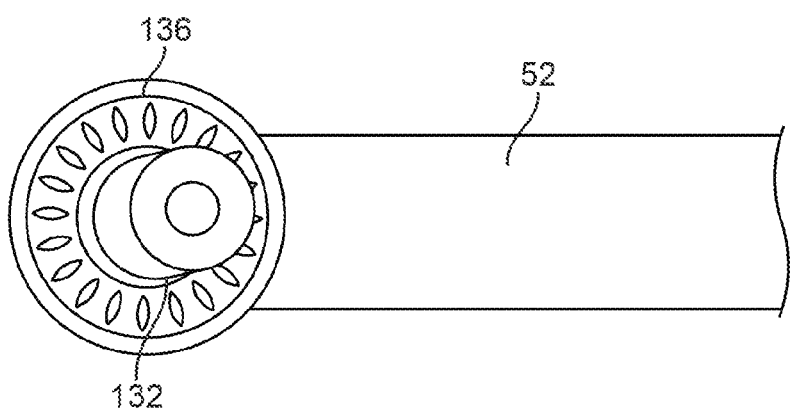

In yet another variation of the support arm, FIGS. 12A and 12B show side and end views of a support arm 52 having a rectangular cross-sectional area and a length of, e.g., about 6-7 inches. An insertion rod 130 may extend perpendicularly from the support arm 52 and may be rotatably inserted within the receiver support 56 of the cradle assembly 24. Likewise, an insertion rod 132 may extend perpendicularly from the support arm 52 in a direction opposite to insertion rod 130 and may be rotatably inserted within connection interface 34 or any one of the other connection interfaces defined within the radial table 14.

An interface collar 134 may also be defined around the insertion rod 132 adjacent to the support arm for contacting against the receiving support 50. One or more contact projections 136 may also project from the interface collar 134 to facilitate rotation of the support arm 52 relative to the connection interface 34 particularly when the weight of the patient's limb LM is bearing down upon the support arm 52.

Figure 13A:
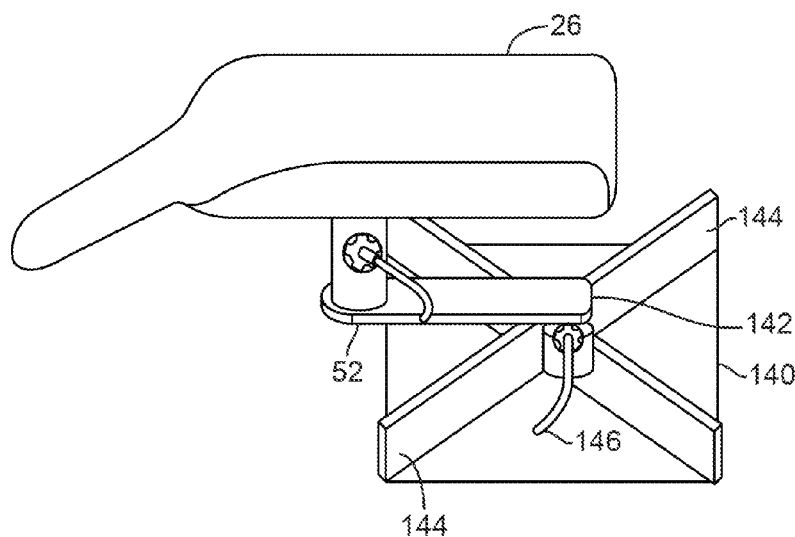
FIGS. 13A and 13B show perspective and assembly views of another variation of a support assembly.
Figure 13B:
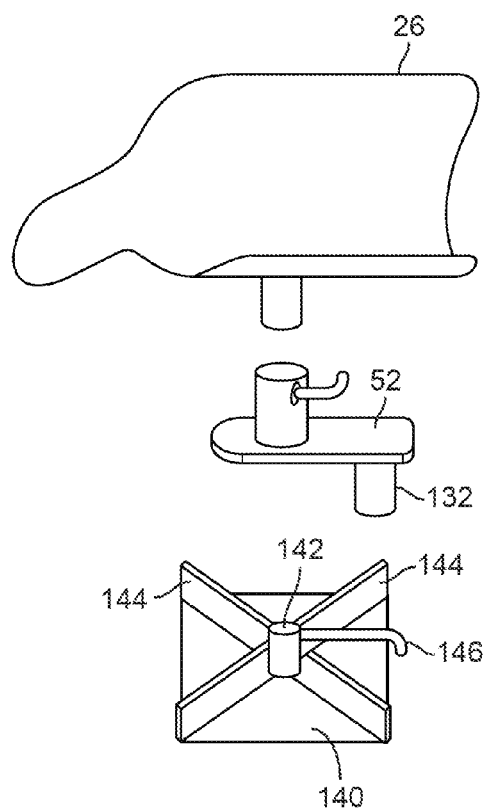
Figure 14:
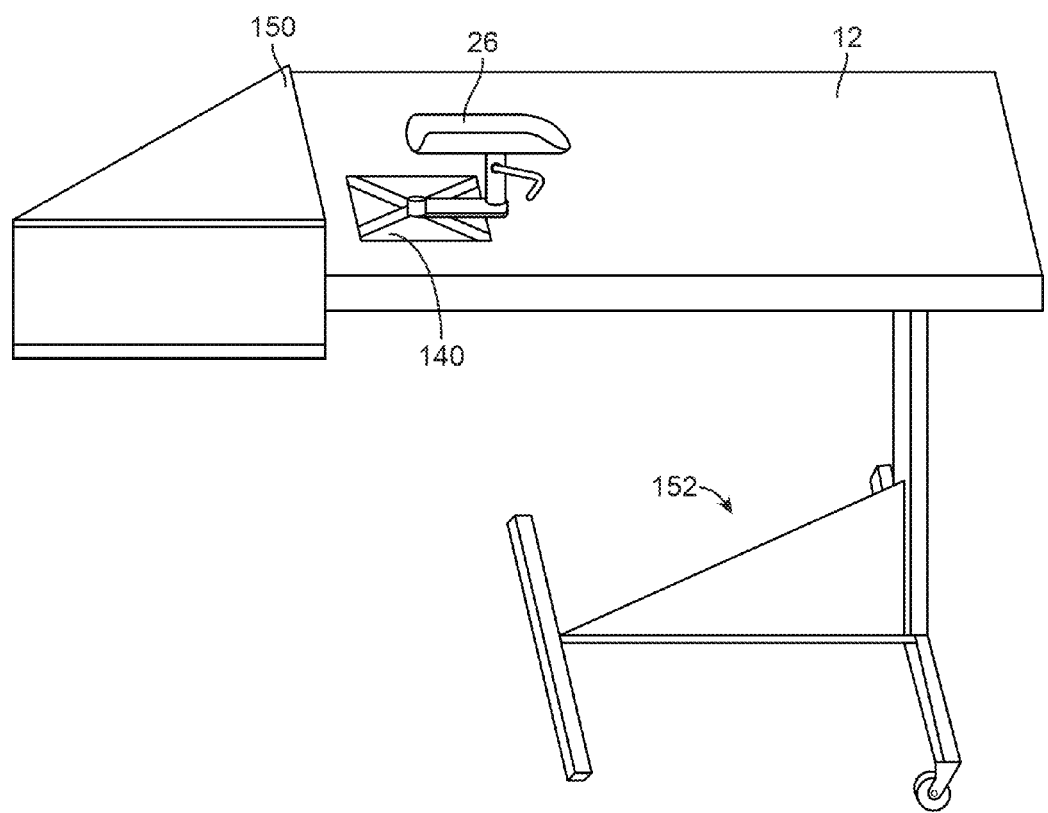
FIG. 14 shows a perspective view of the support assembly of FIG. 13A positioned upon a radial access table.

FIGS. 13A and 13B show perspective and assembly views of yet another variation of the cradle assembly. In this variation, the cradle member 26 and support arm 52 may be rotatingly coupled to a base 140 which is separate from the radial table portion 14. The base 140 shown may have one or more gussets 144 to provide for structural integrity and may further define an insertion rod channel 142 and an optional securement mechanism 146 extending from the insertion rod channel 142. With this variation, the cradle member 26 and base 140 may be positioned upon the radial table or upon another platform. FIG. 14 shows a perspective view of a radial table assembly having the cradle member 26 and base 140 positioned upon the back table 12 supported by a table support 152. The interface portion 150 is radio-lucent and sized to be thicker than the back table 12 in this variation although the thickness of the interface portion 150 may be suitably reduced.

Figure 15A:
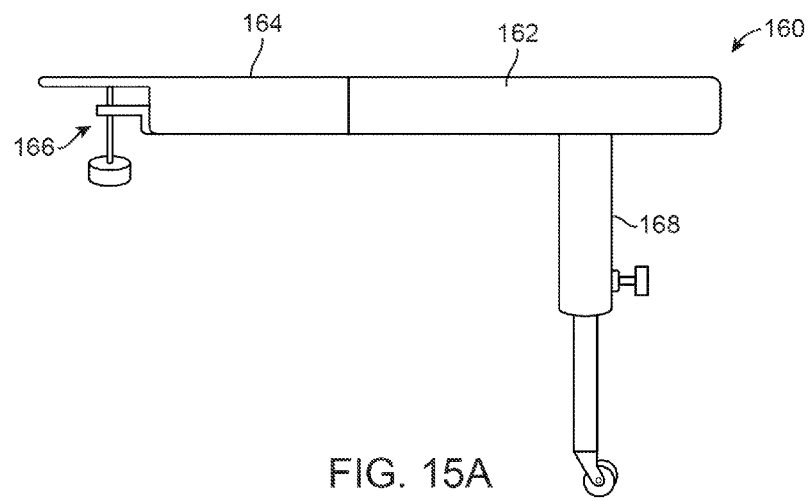
FIGS. 15A and 15B show side and perspective views of yet another variation of the radial access table which may be secured to a catheter laboratory table.
Figure 15B:
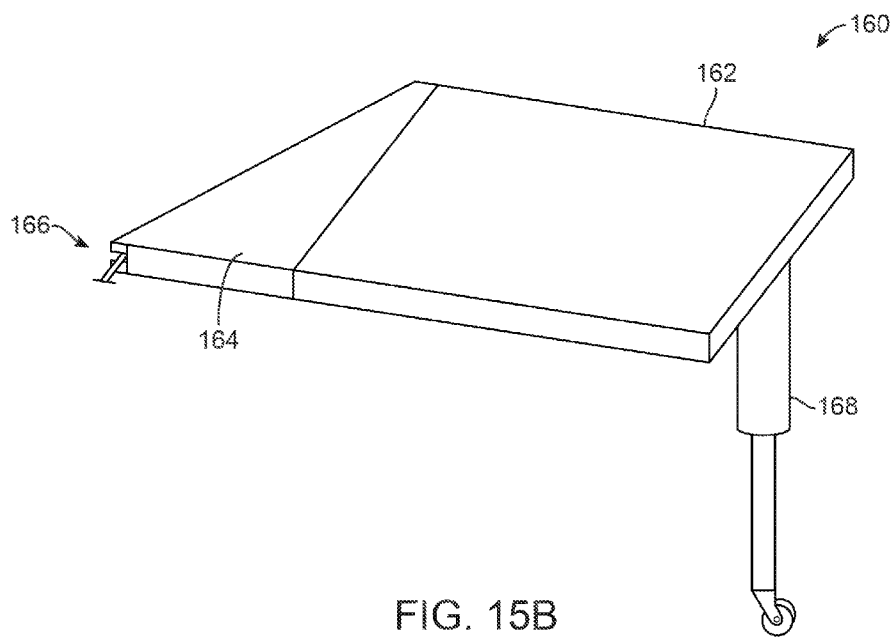
Figure 15C:
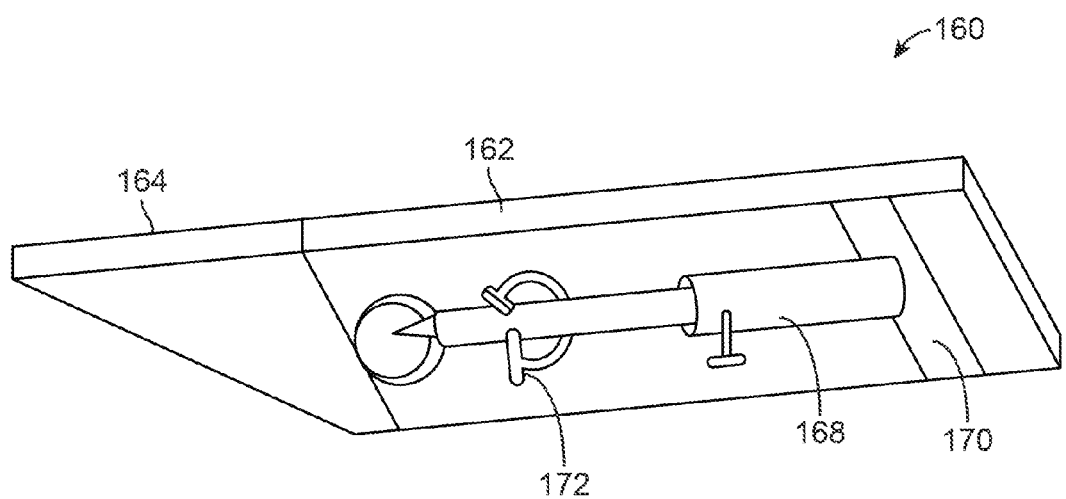
FIG. 15C shows a perspective view of another variation in which a support leg may be pivotably or retractably connected to the radial table.
Figure 15D:
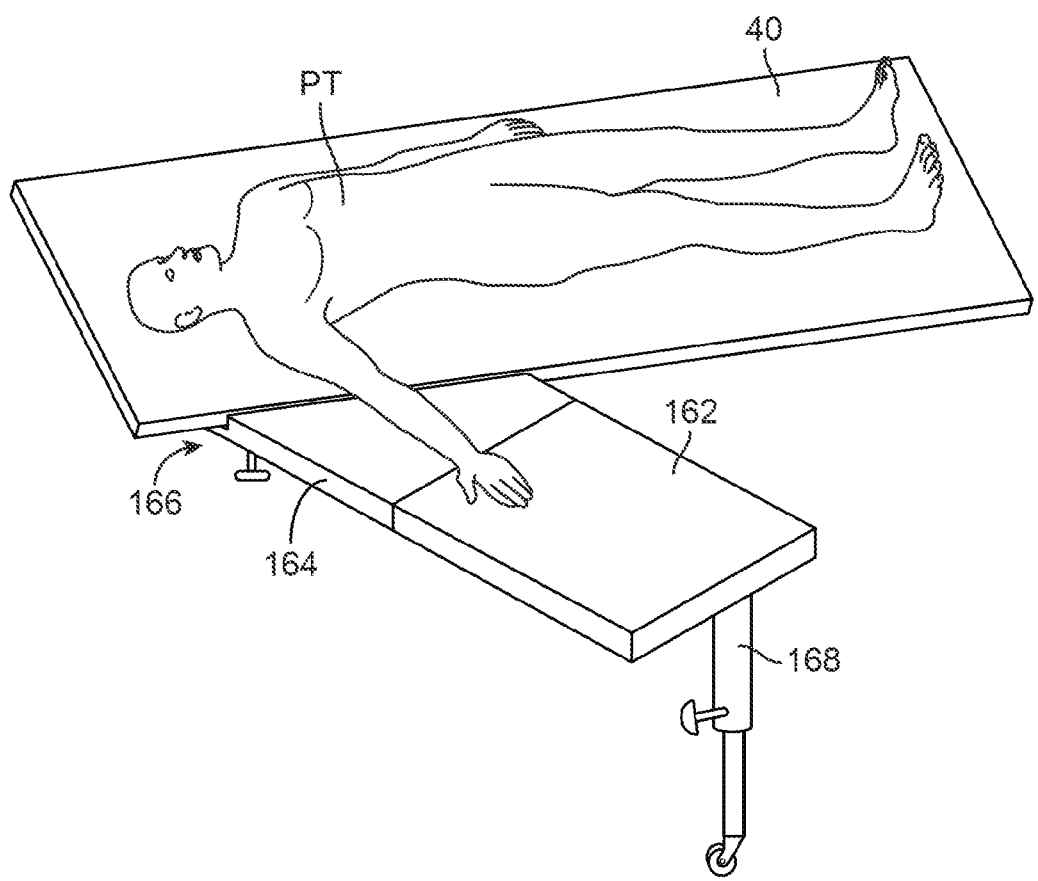
FIG. 15D shows a perspective view illustrating an example of how the table of FIG. 15A may be secured to the catheter laboratory table.

Turning now to the table assembly, FIGS. 15A and 15B show side and perspective views of yet another variation of a radial table assembly 160 generally comprised of a radial table portion 162 and interface portion 164 similar to the other variations. Yet this variation may be configured to be secured or clamped directly to the catheter laboratory table 40 via one or more securement mechanisms 166 (e.g., clamps, etc.) aligned along the angled edge. The distal end of the radial table portion 162 may be supported via a support 168 which may be coupled to the table via an optional retraction or pivoting mechanism 170 which may allow for the support 168 to be pivoted against the table portion 162 and secured by a securement mechanism 172 such as a clamp, as shown in the perspective view of FIG. 15C. FIG. 15D shows a perspective view illustrating how the interface portion 164 may be attached by the securement mechanisms 166 along a side of the laboratory table 40 to extend at an angle. The patient PT may extend their arm along the interface portion 164 to provide for radial access as needed. Also, as the laboratory table 40 moves to reposition the patient relative to an imaging device, the radial table assembly 160 may move with the table 40. With this variation, the cradle assembly may still positioned upon the radial table portion 162 for use as previously described.

Figure 16A:
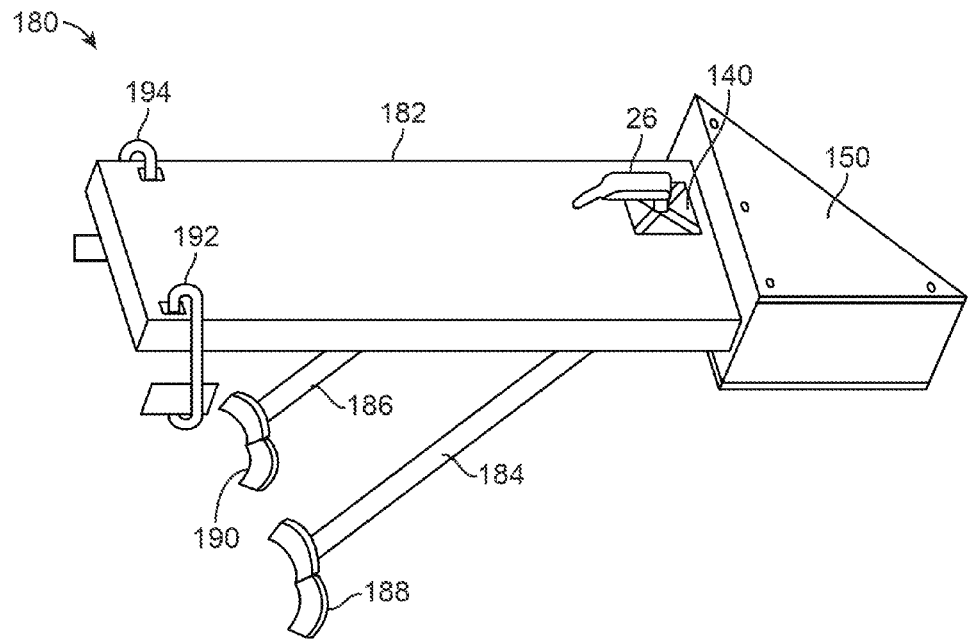
FIGS. 16A and 16B show perspective views of yet another variation of the radial access table which may be clamped or secured to a back table.
Figure 16B:
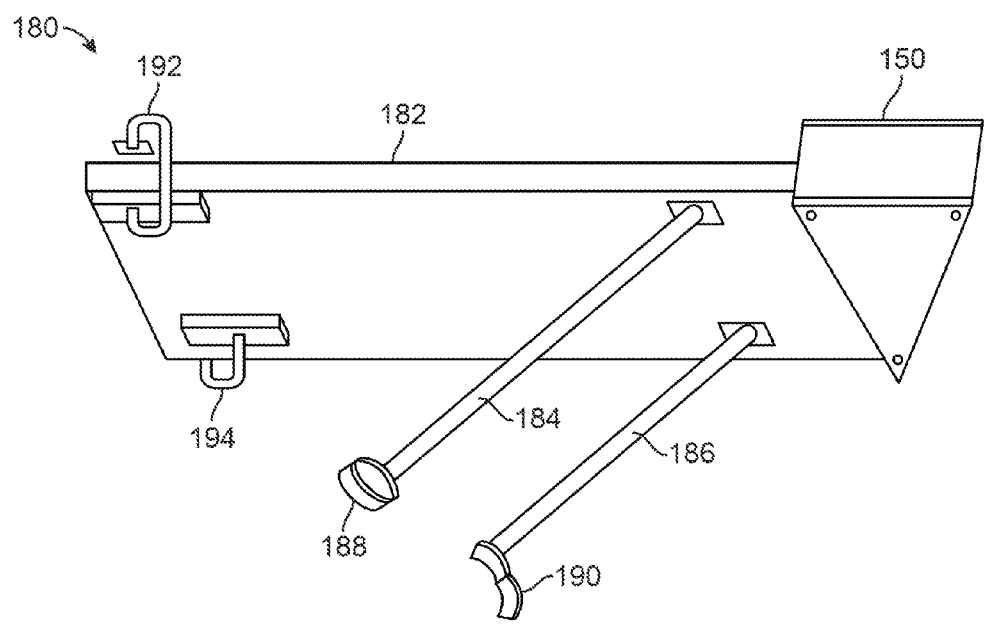
Figure 16C:
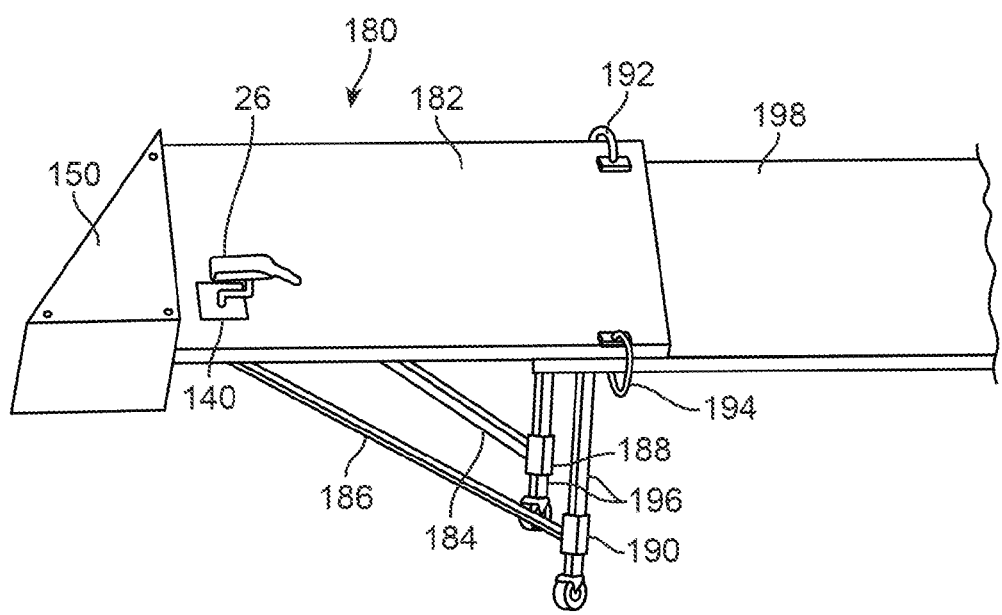
FIGS. 16C and 16D show perspective views of the table of FIG. 16A secured to a back table and positioned in proximity to a catheter laboratory table.
Figure 16D:
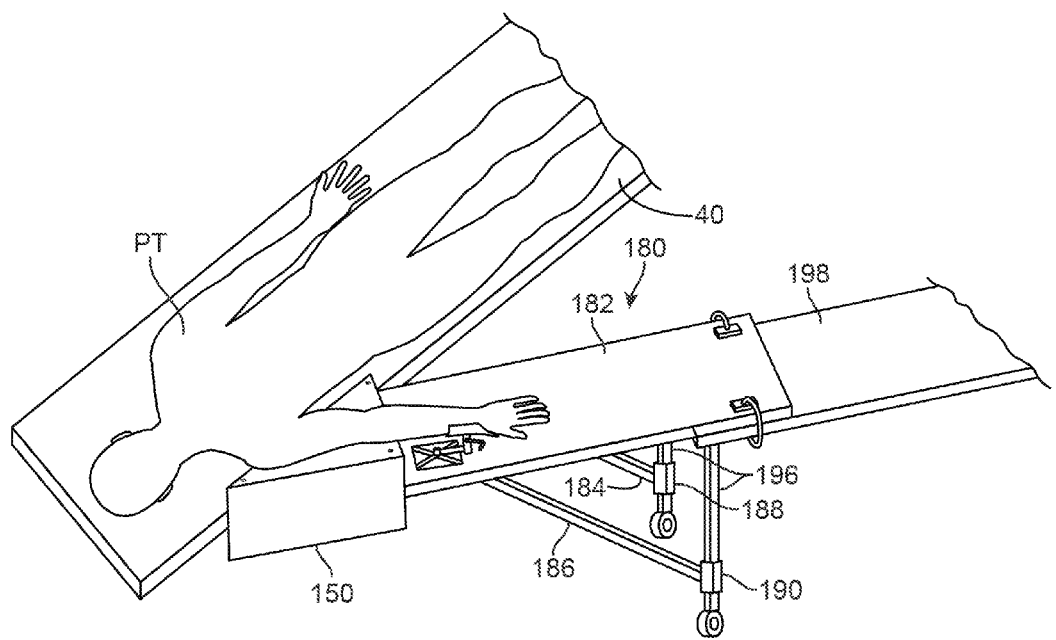

FIGS. 16A and 16B show perspective views of another table assembly variation which may be secured to a separate back table. The radial table assembly 180 shown may generally comprise a radial table 182 having the interface portion 150 and securement mechanisms 192, 194 for securement to the back table as well as support arms 184, 186 which may extend, e.g., at an angle from the radial table 182 for further securement to the legs or supports of the back table via corresponding clamping mechanisms 188, 190. FIG. 16C illustrates how the radial table 182 may be clamped to a separate back table 198 via the securement mechanisms 192, 194. The support arms 184, 186 may also be seen extending from the radial table 182 for attachment to the table legs 196 of the back table 198. In use, as shown in the perspective view of FIG. 16D, the radial table assembly 180 attached to the back table 198 may be placed against the laboratory table 40 with the angled interface portion 150 positioned against the table 40. The cradle assembly may be positioned upon the radial table 182 or other rotatably secured to the radial table 182 for use in the manner described herein with the patient PT.

Figure 17:
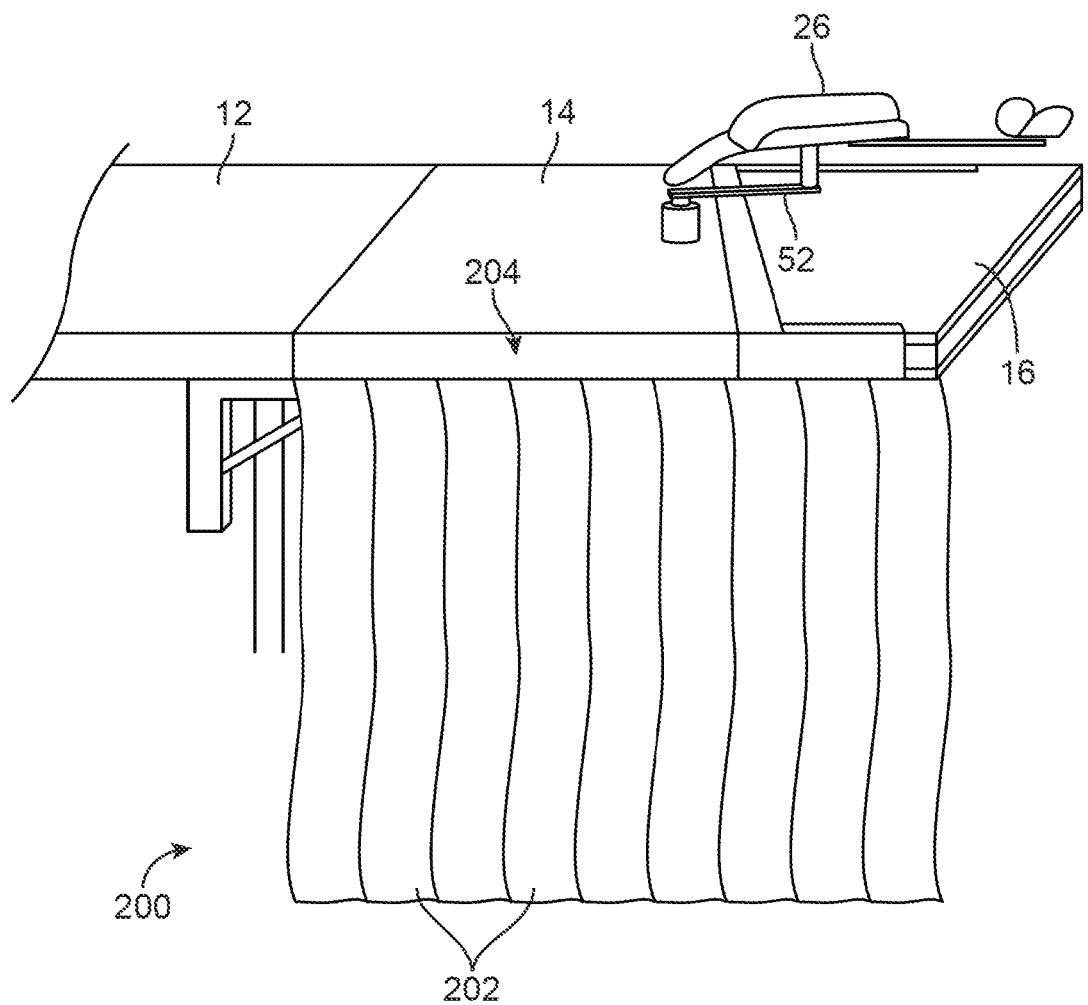
FIG. 17 shows a perspective view of a radial access table incorporating an optional drape or shield.

Aside from the table assembly, additional features and/or accessories may be utilized in combination. One example is shown in the perspective view of FIG. 17 which shows a radiation shield 200 which may be comprised of a single curtain or sheet or a number of individual shielded strips 202 which may be attached along the radial table edge 204. The radiation shield 200 may be attached along any of the edges of the table assembly in proximity to the surgeon or practitioner to provide for additional shielding against, e.g., x-rays, which may be emitted by imaging devices typically used to image the patient's body.

Figure 18:
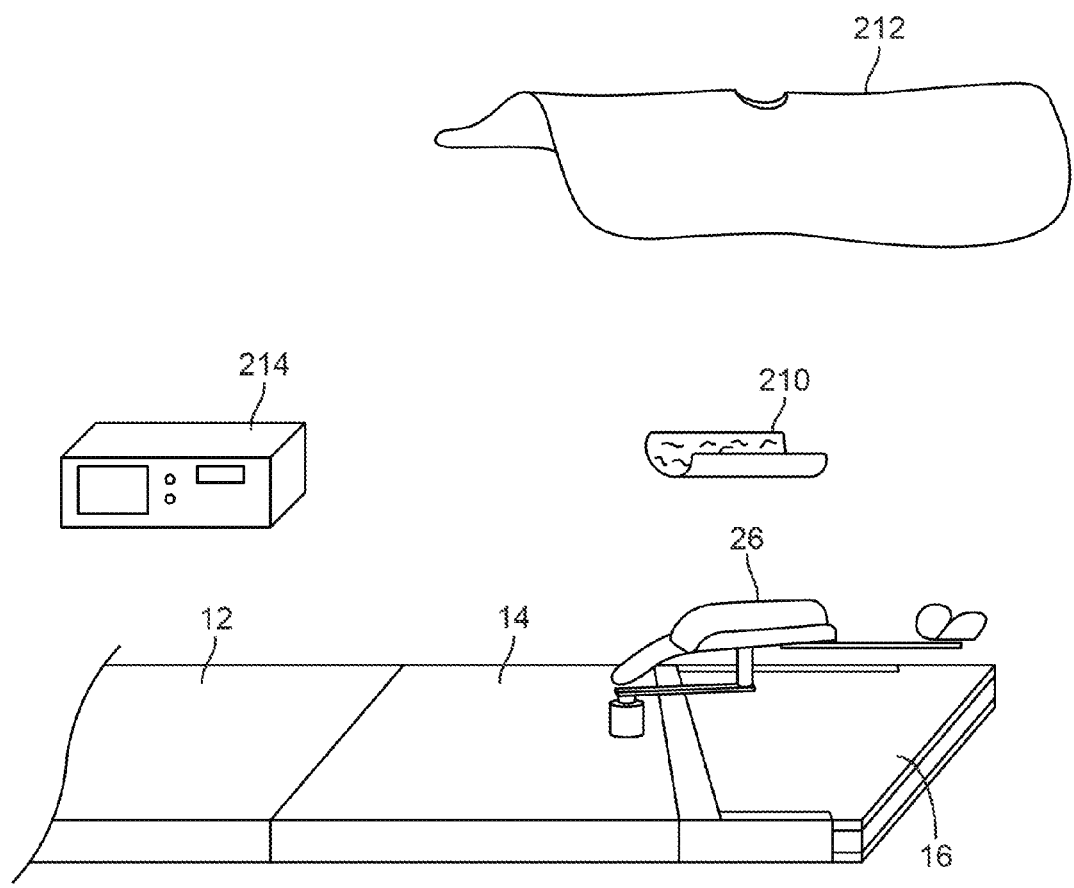
FIG. 18 shows an assembly view of a radial access table and optional accessories which may be specially configured for use with the table.

FIG. 18 shows an assembly view of additional features and/or accessories which may also be used in combination with the radial table assembly. For instance, one or more cushion supports 210 which are configured and shaped for use along the cradle member 26 may be provided with the radial table assembly or separately. Additionally, surgical drapes 212 configured for use with the table assembly or any number of instruments or displays 214 which are positionable upon the back table 12 or radial table 14 may also be provided, if so desired. All or any one of these accessories may be provided in a kit along with the radial table assembly or they may be provided separately.

Moreover, it is further intended that any of the individual features described herein may be utilized in any number of combinations with any other feature as practicable.

The applications of the devices and methods discussed above are not limited to the support of arms but may include any number of further applications. Moreover, such devices and methods may be applied to other portions of the body. Modification of the above-described assemblies and methods for carrying out the invention, combinations between different variations as practicable, and variations of aspects of the invention that are obvious to those of skill in the art are intended to be within the scope of the claims.

What is claimed is:

1. A table assembly, comprising:
   a platform defining a surface which is sized to support a limb of a patient;
   an interface portion extending from a distal end of the platform, wherein the interface portion is radio-lucent and extends at a distance from the platform; and
   a cradle member rotatably connected to the platform at a location proximal to the interface portion, wherein the cradle member remains rotatable relative to the platform while supporting the limb,
   wherein the interface portion has a first edge contacting the distal end of the platform and also a second angled edge opposite to the first edge where the second angled edge is relatively longer than the first edge, and
   wherein the interface portion is rotatably adjustable about a longitudinal axis extending through the interface portion and the platform such that the second angled edge is reconfigurable in an opposite direction when the interface portion is rotated.

2. The assembly of claim wherein the interface portion is configured to be secured with the platform such that further rotation about the longitudinal axis is prevented.

3. The assembly of claim 1 wherein the second angled edge of the interface portion is positionable against either side of an additional platform when the interface portion is reconfigured.

4. The assembly of claim 1 wherein the interface portion extends at the distance which is sized to accommodate an imaging apparatus without interference beneath the interface portion.

5. The assembly of claim 1 wherein the cradle member is configured to receive and support a limb of a patient.

6. The assembly of claim 5 further comprising:
   a connection interface configured to secure the cradle member to the platform; and
   a support arm rotatably extending from the connection interface to the cradle member.

7. The assembly of claim 1 further comprising a radio-opaque barrier extending from the interface portion and/or platform.

8. A table assembly, comprising:
   a platform defining a surface which is sized to support a limb of a patient;
   an interface portion extending from a distal end of the platform, wherein the interface portion has a first edge contacting the distal end of the platform and also a second angled edge opposite to the first edge and where the second angled edge is angled non-perpendicularly relative to the platform in a first orientation,
   wherein the interface portion is radio-lucent and extends at a distance from the platform, and,
   wherein the interface portion is configured to disengage from the platform and reconnect in a rotated configuration relative to the platform such that the second angled edge is reversed relative to the platform in a second orientation which is opposite to the first orientation.

9. The assembly of claim 8 wherein the second angled edge is positionable against either side of an additional platform when the interface portion is in the first or second orientation.

10. The assembly of claim 8 wherein the interface portion extends at the distance which is sized to accommodate an imaging apparatus without interference beneath the interface portion.

11. The assembly of claim 8 further comprising a cradle member configured to receive and support a limb of a patient and rotatably connected to the platform at a location proximal to the interface portion.

12. The assembly of claim 11 further comprising:
    a connection interface configured to secure the cradle member to the platform; and
    a support arm rotatably extending from the connection interface to the cradle member.

13. The assembly of claim 8 further comprising a radio-opaque barrier extending from the interface portion and/or platform.

14. A support assembly, comprising:
    a cradle member which is configured to receive and support a limb of a patient:
    a connection interface configured to rotatably secure the assembly to a first platform;
    an interface portion attached at a distal end of the first platform, wherein the interface portion is radio-lucent and extends at a distance from the first platform;
    a second platform upon which the patient is positionable, wherein the second platform is separated from the first platform; and,
    a support arm rotatably extending from the connection interface and rotatably coupled to the cradle member,
    wherein the cradle member is rotatable relative to the first platform and remains rotatable relative to the first platform while supporting the limb, wherein a position and an orientation of the cradle member is dependent upon a position and an orientation of a second platform when the limb is extended from the second platform and is supported upon the cradle member,
    wherein the interface portion has a first edge contacting the distal end of the first platform and also a second angled edge opposite to the first edge where the second angled edge is relatively longer than the first edge, and
    wherein the interface portion is rotatably adjustable about a longitudinal axis extending through the interface portion and the first platform such that the second angled edge is reconfigurable in an opposite direction when the interface portion is rotated.

15. The assembly of claim 14 wherein the position and the orientation of the cradle member is dependent upon the position and the orientation of the second platform via the limb extending between the first platform and the second platform.

16. The assembly of claim 14 further comprising:
   a first pivot rotatingly coupled between the connection interface and a proximal end of the support arm; and
   a second pivot rotatingly coupled between the cradle member and a distal end of the support arm.

17. The assembly of claim 14 wherein the interface portion is configured to be secured with the first platform such that further rotation about the longitudinal axis is prevented.

18. The assembly of claim 14 wherein the interface portion is further configured to be retractably folded relative to the first platform.

19. The assembly of claim 14 wherein the second angled edge of the interface portion is positionable against either side of the second platform when the interface portion is reconfigured.

20. The assembly of claim 17 wherein the interface portion extends at the distance which is sized to accommodate an imaging apparatus without interference beneath the interface portion.

21. The assembly of claim 17 further comprising a radio-opaque barrier extending from the interface portion and/or platform.

22. A method of positioning a patient body, comprising:
   positioning a first platform in proximity to a second platform upon which the patient body is placed, where the first platform is separated from the second platform;
   maintaining a distance between the first platform and the second platform via an interface portion extending from the first platform, the interface portion having a first edge contacting a distal end of the first platform and also a second angled edge opposite to the first edge where the second angled edge is relatively loner than the first edge:
   securing a limb of the patient body upon a cradle member which is movably attached to the first platform;
   repositioning the second platform upon which the patient body is placed and from which the limb is extended while maintaining the first platform in a static position relative to the second platform; and
   rotating the cradle member relative to the first platform via the limb extending from the second platform in a manner corresponding, to a repositioning movement of the second platform.

23. The method of claim 22 further comprising imaging the body via an imager while moving the second platform.

24. The method of claim 22 further comprising positioning a radio-lucent interface portion beneath a portion of the limb prior to moving the cradle member, where the interface portion is attached at a distal end of the first platform.

25. The method of claim 22 wherein positioning a first platform further comprises rotatably adjusting the interface portion about a longitudinal axis extending through the interface portion and the platform.

26. The method of claim 22 wherein repositioning the second platform comprises rotating the cradle member relative to the first platform via a connection interface rotatably attached at a distal end of the first platform.

27. The method of claim 26 further comprising rotating the cradle member relative to the first platform via a support arm rotatably extending from the connection interface to the cradle member.

\* \* \* \* \*